United States Patent [19]
Lin

[11] Patent Number: 5,823,208
[45] Date of Patent: Oct. 20, 1998

[54] TOOTHPICK STRUCTURE

[75] Inventor: Ching Hsi Lin, Changhua Hsien, Taiwan

[73] Assignee: Chien I Industry Co., Ltd., Changhua Hsien, Taiwan

[21] Appl. No.: 865,877

[22] Filed: May 30, 1997

[51] Int. Cl.[6] .................................................. A61C 15/02
[52] U.S. Cl. .......................................................... 132/329
[58] Field of Search .................................... 132/329, 321, 132/323; 433/142, 141, 143

[56] References Cited

U.S. PATENT DOCUMENTS

| | | | |
|---|---|---|---|
| 1,397,395 | 11/1921 | Bixler | 433/143 |
| 1,982,285 | 11/1934 | Bronner | 433/142 |
| 4,314,574 | 2/1982 | Inerte | 132/329 |
| 4,832,061 | 5/1989 | Hwang | 433/141 |
| 5,230,356 | 7/1993 | Villas | 132/329 |
| 5,588,452 | 12/1996 | Peck | 132/329 |

FOREIGN PATENT DOCUMENTS

| | | | |
|---|---|---|---|
| 604677 | 9/1978 | Switzerland | 132/329 |
| 2130099 | 5/1984 | United Kingdom | 433/143 |

*Primary Examiner*—Todd E. Manahan
*Assistant Examiner*—Eduando C. Robert
*Attorney, Agent, or Firm*—Browdy and Neimark

[57] ABSTRACT

A flexible integrally produced toothpick structure for gum massaging and teeth cleaning purpose has one end provided with a fixed reverse U-shaped end having, parallel rung elements or cross elements disposed thereon or arc-shaped outward projections defined consecutively or alternatively on either side thereof. The reverse U-shaped end can be twisted in use so as to effectively bring out food residues stuck in between teeth. The opposite end of the toothpick is provided with a flat extension on which are disposed a number of V-shaped marks for massaging the gum; and a slant pointed projection in connection to the flat extension is used to pick out food residues left between molar teeth.

4 Claims, 3 Drawing Sheets

TOOTHPICK STRUCTURE

BACKGROUND OF THE INVENTION

The present invention relates to a flexible integral toothpick structure for gum massaging and teeth cleaning purpose having one end provided with a reverse U-shaped end having parallel rung elements or cross elements disposed thereon or are-shaped outward projections defined consecutively or alternatively on either side thereof. The reverse U-shaped end can be twisted in use so as to effectively bring out food residues stuck in between teeth. The opposite end of the toothpick is provided with a flat extension on which are disposed a number of V-shaped depressed marks for massaging the gum; and a slanted pointed projection in connection to the flat extension is used to pick out food residues left between molar teeth.

Generally, common toothpicks are provided with a pointed picking end and a round end or two pointed picking ends which are used to clean up food residues stuck between teeth. Such toothpicks are smooth on their surfaces and have less contact area when inserted between teeth, so they are not very effective in picking out food residues left in small holes between teeth. Besides, the cone-shaped pointed end can hurt the dental gum easily and make the fissures between teeth widened.

SUMMARY OF THE INVENTION

Therefore, the primary object of the present invention is to provide a flexible integrally produced toothpick which has a fixed reverse U-shaped end having parallel rung elements or cross elements or arc-shaped projections consecutively or alternatively disposed on either side thereof, the U-shaped end can be inserted into fissures between teeth and he twisted in use so as to effectively clean up food residues left between teeth.

Another object of the present invention is to provide a flexible integrally produced toothpick which has the other end provided with a flat extension on which V-shaped marks for massaging dental gum are defined; and a slanted pointed projection which can be easily inserted into fissures between molar teeth is connected to the flat extension.

BRIEF DESCRIPTION OF THE DRAWINGS

Referring to FIG. 1, the flexible toothpick of the present invent ion is integrally produced by plastics injection molding art. In a first embodiment, the flexible toothpick body 10 has a fixed reverse U-shaped end 11 provided with a number of parallel rung elements 12 which can be inserted into fissures between teeth in use. The opposite end of the toothpick body 10 is provided with a flat extension 13 in connection to a slanted pointed projection 14. On both surface of the flat extension 13 are defined a number of V-shaped depressed marks 15. Alternatively, the V-shaped marks can be made as projections from the surface of projection 14.

As shown in FIG. 2, the reverse U-shaped end 11 along with the parallel rung elements 12 can be inserted in the fissures between teeth with ease and they can be further twisted so as to bring out food residues stuck between teeth effectively.

Referring to FIG. 3, the slanted pointed end 14 in connection to the flat extension 13 of the toothpick of the present invention is inserted into the fissures between the rear molar teeth for easily cleaning food residues and to place the V-shaped marks 15 on the flat extension 14 against the gum for massaging.

Figure 1:
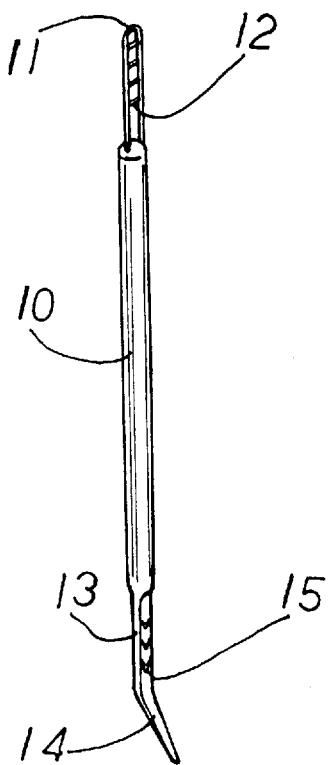
FIG. 1 is a perspective diagram of the present invention.
Figure 2:
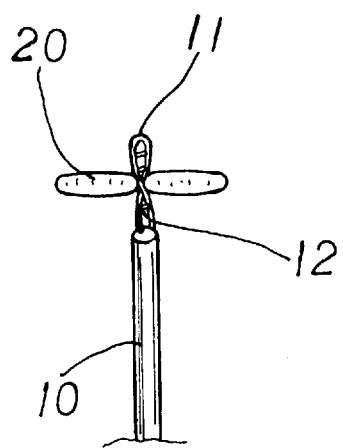
FIG. 2 is a diagram illustrating a practical application of the toothpick of the Present invention.
Figure 3:
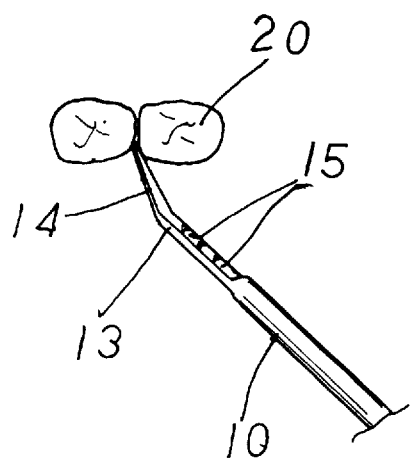
FIG. 3 is a diagram showing the application of the pointed end of the toothpick between two molar teeth.
Figure 4:
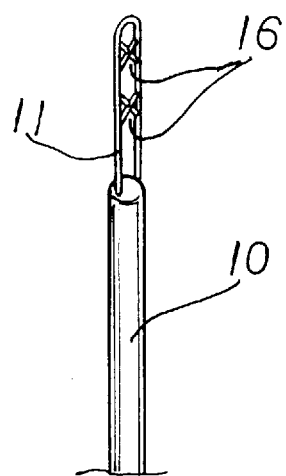
FIG. 4 is a diagram showing a second embodiment of the present invention.
Figure 6:
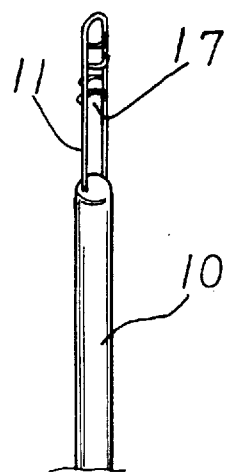
FIG. 6 is a diagram showing a fourth embodiment of the present invention.

Referring further to FIG. 4, the second embodiment. of the present invention is illustrated wherein the reverse U-shaped end 11 is provided with cross-shaped element 16.

Figure 5:
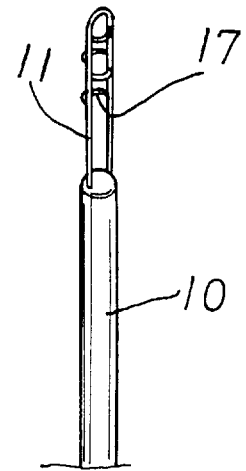
FIG. 5 is a diagram showing a third embodiment of the present invention.

Referring to FIG. 5, the third embodiment of the present invention is provided with a reverse U-shaped end 11 having an arc-shaped projection disposed alternatively on each side thereof.

Furthermore, the fourth embodiment of the present invention, as shown in FIG. 5, is given wherein the reverse U-shaped end 11 is provided with two consecutive arc-shaped projections 17 on one side and two consecutive arc-shaped projections on the other side of the reverse U-shaped end 11.

It can be clearly seen that the reverse U-shaped end 11 with either parallel rung elements 12 or crossed elements 16 can be twisted when inserted into the fissure between two teeth so as to effectively bring out food residues left in the fissure. The outward projections 17 on either side of the reverse U-shaped end 11 can be more effective in clearing the food residues left between the teeth 20.

I claim:

1. An toothpick structure integrally produced by plastics injection molding having a flexible toothpick body being characterized by that:

said toothpick body having a fixed reverse U-shaped first end provided with a number of parallel rung elements thereon:

a second end of said toothpick body being provided with a flat extension on which V-shaped marks for massaging dental gum are defined; and a slanted pointed projection connected to said flat extension wherein said fixed reverse U-shaped end can be inserted into fissures between teeth and be twisted for effectively cleaning up food residues stuck between teeth, and said slanted pointed projection can be easily inserted into fissures between molar teeth.

2. The toothpick structure as claimed in claim 1 wherein said number of parallel rung elements are arc-shaped protrusions alternately protruding from each side of said fixed reverse U-shaped end.

3. The toothpick structure as claimed in claim 1 wherein said number of parallel rung elements are arc-shaped protrusions alternately protruding in pairs from each side of said fixed reverse U-shaped end.

4. An toothpick structure integrally produced by plastics injection molding having a flexible toothpick body being characterized by that:

said toothpick body having a fixed reverse U-shaped first end provided with a number of cross-shaped elements thereon:

a second end of said toothpick body being provided with a flat extension on which V-shaped marks for massaging dental gum are defined; and a slanted pointed projection connected to said flat extension, wherein said fixed reverse U-shaped end can be inserted into fissures between teeth and be twisted for effectively cleaning up food residues stuck between teeth, and said slanted pointed projection can be easily inserted into fissures between molar teeth.

\* \* \* \* \*